US009083546B2

(12) United States Patent
Sadhu

(10) Patent No.: US 9,083,546 B2
(45) Date of Patent: Jul. 14, 2015

(54) SYSTEM AND METHOD FOR COMMUNICATING HEALTH PARAMETERS OF AN OCCUPANT IN AN AUTOMOBILE AND A DYNAMIC OPERATION OF THE AUTOMOBILE AND HOME AUTOMATION

(76) Inventor: Rajendra Padma Sadhu, Somerset, NJ (US)

( * ) Notice: Subject to any disclaimer, the term of this patent is extended or adjusted under 35 U.S.C. 154(b) by 356 days.

(21) Appl. No.: 13/361,982

(22) Filed: Jan. 31, 2012

(65) Prior Publication Data

US 2013/0303131 A1    Nov. 14, 2013

(51) Int. Cl.
| | |
|---|---|
| H04L 12/28 | (2006.01) |
| H04L 29/08 | (2006.01) |
| H04L 12/40 | (2006.01) |
| H04W 4/00 | (2009.01) |
| H04W 84/00 | (2009.01) |
| A61B 5/00 | (2006.01) |
| A61B 5/01 | (2006.01) |
| A61B 5/0205 | (2006.01) |
| A61B 5/021 | (2006.01) |
| A61B 5/024 | (2006.01) |
| A61B 5/0404 | (2006.01) |
| A61B 5/08 | (2006.01) |
| A61B 5/11 | (2006.01) |
| A61B 5/117 | (2006.01) |
| A61B 5/145 | (2006.01) |
| H04W 4/04 | (2009.01) |

(52) U.S. Cl.
CPC .......... *H04L 12/2825* (2013.01); *A61B 5/0022* (2013.01); *A61B 5/0205* (2013.01); *A61B 5/1112* (2013.01); *A61B 5/1176* (2013.01); *A61B 5/7465* (2013.01); *A61B 5/01* (2013.01); *A61B 5/021* (2013.01); *A61B 5/02438* (2013.01); *A61B 5/0404* (2013.01); *A61B 5/0816* (2013.01); *A61B 5/14532* (2013.01); *H04L 67/12* (2013.01); *H04L 2012/40273* (2013.01); *H04W 4/046* (2013.01); *H04W 84/005* (2013.01)

(58) Field of Classification Search
CPC .... H04W 4/046; H04W 84/005; H04L 67/12; H04L 2012/40273; H04L 12/2825; A61B 5/7465; A61B 5/1112; A61B 5/14532; A61B 5/0022; A61B 5/01; A61B 5/0816; A61B 5/02438; A61B 5/021; A61B 5/0404; A61B 5/0205; A61B 5/1176
USPC ................ 455/41.1, 41.2, 403, 404.1, 404.2, 455/414.1, 418, 423, 425, 456.1, 557, 455/569.1, 569.2, 575.9
See application file for complete search history.

(56) References Cited

U.S. PATENT DOCUMENTS

| | | | |
|---|---|---|---|
| 2010/0017759 A1* | 1/2010 | Birnbaum et al. ............ 715/863 |
| 2010/0234692 A1* | 9/2010 | Kuo et al. .................... 600/300 |
| 2010/0235454 A1* | 9/2010 | Holden et al. ................ 709/206 |
| 2013/0048809 A1* | 2/2013 | Jacobson ................... 248/206.2 |

* cited by examiner

*Primary Examiner* — Dinh P Nguyen
(74) *Attorney, Agent, or Firm* — Maier & Maier, PLLC

(57) ABSTRACT

System and method for communicating health parameters of an occupant in an automobile and a dynamic operation of the automobile and home automation are disclosed. The system includes a functional device configured to (a) reading and relaying health parameters from authorized occupant in the automobile (b) receive and relay commands from the authorized occupant for an automated operation of the automobile (b) reading and relaying signals from a home automation server connected to at least one sensor positioned at a predetermined location and (c) reading and relaying a plurality of signals from a home automation server, whereby the home automation server connected to at least one sensor positioned at a predetermined location. The system further includes an automobile management module positioned in the automobile to operate the automobile and to customize the functionalities associated to the automobile and a home automation in communication with the home automation sensors.

17 Claims, 2 Drawing Sheets

SYSTEM AND METHOD FOR COMMUNICATING HEALTH PARAMETERS OF AN OCCUPANT IN AN AUTOMOBILE AND A DYNAMIC OPERATION OF THE AUTOMOBILE AND HOME AUTOMATION

TECHNICAL FIELD OF THE INVENTION

The present invention generally relates to a remote health monitoring and automated vehicle management system. More particularly, the present invention relates to a system and method for communicating health parameters of an occupant in an automobile and an automated operation of the automobile and also a home automation system.

BACKGROUND OF THE INVENTION

Generally, motor vehicles include a variety of electronic devices for convenience and safety. Among them few cars and other vehicles provide automatic climate system to maintain a set temperature for the driver and passenger and also provide an automatic lighting system to illuminate interior of the vehicle and control external lights of the vehicle. Even many convenience features such as seat adjustments, steering wheel adjustments, automatic mirrors, and the like provide additional convenience for drivers and passengers. Also other features such as intelligent airbags are able to discriminate children from adults to prevent deployment for further safety.

Conventionally, vehicle security is based on keys and key codes for starting the engine or accessing secure compartments such as the trunk or glove compartment. The vehicle settings are manually adjusted to the users comfort level but these settings can be changed by the other user according to his comfort level and the first user has to again readjust the settings manually for his comfort. Thus frequently adjusting the settings of the vehicle is a disadvantage for the system to have convenience in vehicle.

Typically, medical diagnosis in motor vehicles is known in ambulance which is equipped with all the devices necessary for the purpose of providing health care to the patient in the mean while of reaching him to a health centre. Even for further advancement of medically treating an occupant in motor vehicle is equipped with a therapeutic heat cushion for a seat connected to the cigarette lighter in the motor vehicle which can be installed and started by the occupant. So, the present system is also disadvantageous for using manual interference for operating the medical diagnosis in motor vehicle.

Typically, people tend to forget to remember if a garage door is closed and even forget to remember if the lights in a house/home/Office or any building are switched off. The conventionally existing technologies describe about a remotely operated mechanisms. There is no current mechanism available in the automobile that displays the status of the doors and windows in the car and issue a command to close the door or windows when they are in far away from the building or office.

In the light of aforementioned limitations, there exits a need for a wireless communication system to be established in a motor vehicle and enable a communication with the central monitoring station through GPRS, WCDMA, EDGE, UMTS, HSDPA, Wi-Fi, WiMax on a GSM/CDMA device with GPS modules for monitoring health parameters, sharing the internet in car, remotely issuing/reading data from the automobile or to home automation gateway which is connected to sensors, issuing commands and reading data from patients and face detection system in a wireless sensor network and even a built in camera to talk to remote doctor/technician/person for help and guidance or view a camera which is connected at home remotely from the car.

BRIEF SUMMARY OF THE INVENTION

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

Exemplary embodiments of the present invention are directed towards an interactive system for communicating health parameters of an occupant in an automobile and a dynamic operation of the automobile and home automation. According to a first aspect, the system includes an functional device configured to (a) reading and relaying a plurality of health parameters from at least one authorized occupant in the automobile (b) receive and relay a plurality of commands from the at least one authorized occupant for an automated operation of the automobile (b) reading and relaying a plurality of signals from a home automation server, whereby the home automation server connected to at least one sensor positioned at a predetermined location and (c) reading and relaying a plurality of signals from a home automation server, whereby the home automation server connected to at least one sensor positioned at a predetermined location. The functional device includes a key pad to dial a contact number and to pair with the authenticated mobile device. The functional device configured to receive an automobile activation signal from the authenticated mobile device to customize the plurality of functional functionalities associated to the automobile and to generate at least one alert corresponding to the plurality of functional functionalities associated to the automobile. The functional device includes an image capturing module to detect the at least one authorized occupant and communicate with the health monitoring station. The functional device is portable or can be inbuilt in the automobile or can be hanged in the automobile or can be fixed in the interior of the automobile through a suction means. A software application is configured in the authenticated mobile device to generate the automobile activation signal for transmitting to the functional device. The functional device configured to serve as a router enabling the at least one authorized occupant to access internet, to transmit a functional status of a plurality of embodiments of the automobile to a centralized server, to read health parameters from at least one medical device worn by the at least one occupant. The medical device communicates with the functional device through a short wireless network.

According to the first aspect, the system includes a cellular data communication module inbuilt in the functional device for transmitting the plurality of health parameters to a remote health monitoring station over a communication network.

According to the first aspect, the system includes an automobile management module positioned in the automobile to operate the automobile and in communication with the functional device configured to customize a plurality of functional functionalities associated to the automobile. The communication between the functional device and the automobile management module includes a wired communication or a short range wireless network.

According to a second aspect, a functional device for communicating health parameters of an occupant in an automobile and a dynamic operation of the automobile and home automation includes a health parameter data capturing module for reading and relaying a plurality of health parameters from at least one authorized occupant in the automobile.

According to the second aspect, the functional device includes a cellular data communication module inbuilt in the functional device for transmitting the plurality of health parameters to a remote health monitoring station over a communication network.

According to the second aspect, the functional device includes a key pad to dial a contact number and to pair with an authenticated mobile device. The keypad may include a virtual keypad or a physical keypad.

According to the second aspect, the functional device includes an alerting unit configured to generate at least one alert corresponding to the plurality of functional functionalities associated to the automobile.

According to the second aspect, the functional device includes an image capturing module to detect the at least one authorized occupant and authenticating the at least one occupant to communicate with the health monitoring station.

According to the second aspect, the functional device includes a router module enabling the at least one authorized occupant to access an internet.

According to the second aspect, the functional device includes an automobile activation module configured to receive an activation signal from an authenticated mobile device to customize a plurality of functional functionalities associated to the automobile.

According to the second aspect, the functional device includes an automation control unit for reading and relaying a plurality of signals from a home automation server, whereby the home automation server connected to at least one sensor positioned at a predetermined location.

According to the second aspect, the functional device includes a means to communicate with the automobile management module configured to operate the automobile and to customize a plurality of functional functionalities associated to the automobile.

According to a third aspect, a method for communicating health parameters of an occupant in an automobile and a dynamic operation of the automobile and home automation includes reading and relaying a plurality of health parameters from at least one authorized occupant in the automobile, receiving and relaying a plurality of commands from the at least one authorized occupant for an automated operation of the automobile, a reading and relaying a plurality of signals from a home automation server, whereby the home automation server connected to at least one sensor positioned at a predetermined location by a functional device.

According to the third aspect, the method includes transmitting the plurality of health parameters to a remote health monitoring station over a communication network by a cellular data communication module inbuilt in the functional device.

According to the third aspect, the method includes receiving an activation signal from the functional device by a automobile module for customizing a plurality of functional functionalities associated to the automobile in communication with the functional device, whereby the automobile management device positioned in the automobile.

BRIEF DESCRIPTION OF THE DRAWINGS

Other objects and advantages of the present invention will become apparent to those skilled in the art upon reading the following detailed description of the preferred embodiments, in conjunction with the accompanying drawings, wherein like reference numerals have been used to designate like elements, and wherein.

DETAILED DESCRIPTION OF THE INVENTION

Figure 1:
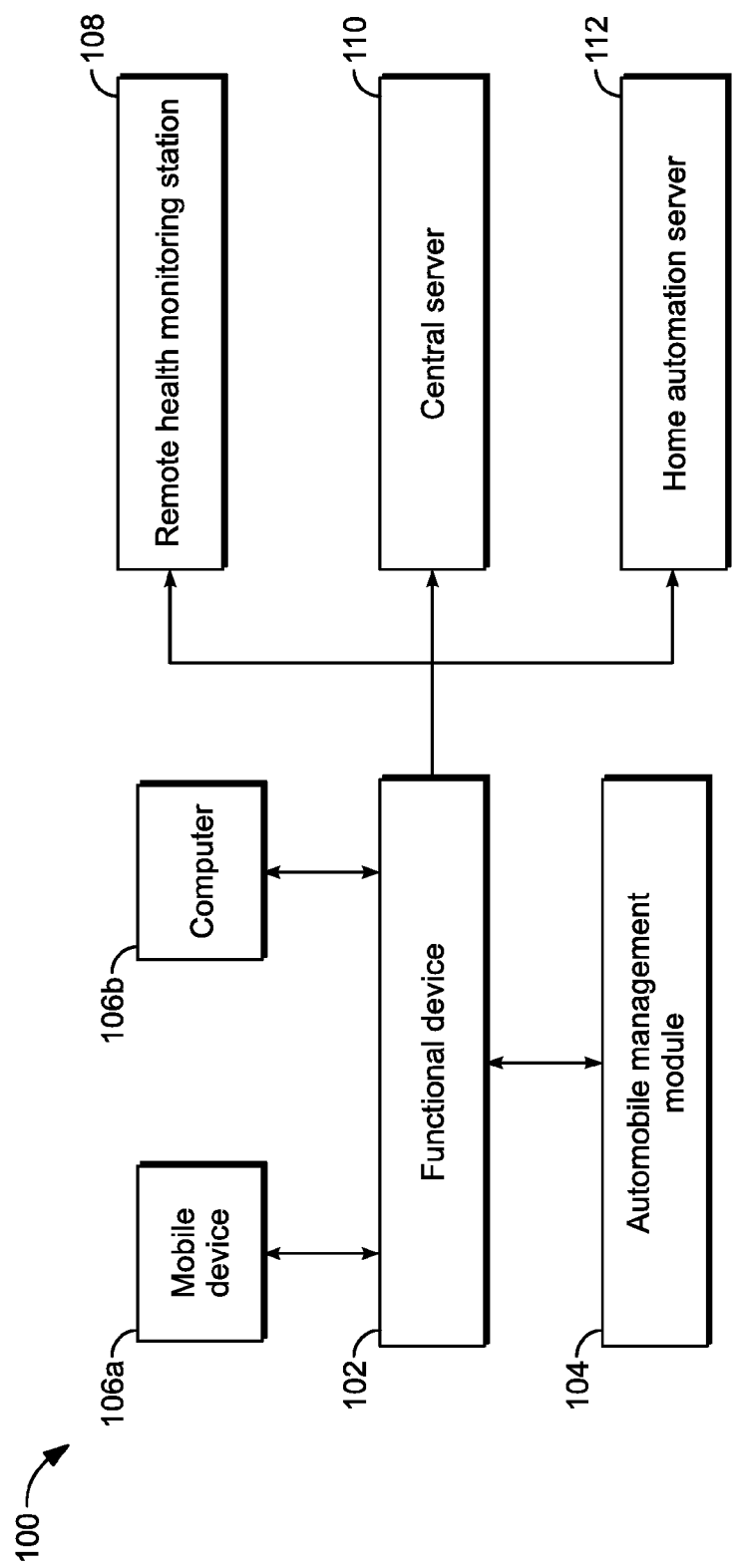
FIG. 1 is a diagram depicting an over view of a system for communicating health parameters of an occupant and a dynamic operation of the automobile and home automation.

It is to be understood that the present disclosure is not limited in its application to the details of construction and the arrangement of components set forth in the following description or illustrated in the drawings. The present disclosure is capable of other embodiments and of being practiced or of being carried out in various ways. Also, it is to be understood that the phraseology and terminology used herein is for the purpose of description and should not be regarded as limiting.

The use of "including", "comprising" or "having" and variations thereof herein is meant to encompass the items listed thereafter and equivalents thereof as well as additional items. The terms "a" and "an" herein do not denote a limitation of quantity, but rather denote the presence of at least one of the referenced item. Further, the use of terms "first", "second", and "third", and the like, herein do not denote any order, quantity, or importance, but rather are used to distinguish one element from another.

Referring to FIG. 1 is a diagram 100 depicting an over view of a system for communicating health parameters of an occupant and a dynamic operation of the automobile and home automation. According to a non limiting exemplary embodiment of the present subject matter, the system includes a functional device 102 in communication with an automobile management module 104. The functional device 102 and the automobile management module 104 are positioned in the automobile. The automobile management module 104 may include a zigeebe module, a Bluetooth module, ZigBee or ZWave and the like. The functional device 102 is configured to recognize the occupants in the automobile and read the health parameters of one or more occupants wearing the medical devices. The medical devices may include electronic gadgets capable of operating in a short range wireless communication network. The health parameters of the occupants are transmitted to the remote health monitoring station 108 by a cellular data communication device positioned in the functional device 102. The cellular data communication device may include but not limited to a GPRS, WCDMA, EDGE, UMTS, HSDPA, Wi-Fi, WiMax or a GSM/CDMA device. The functional device 102 may further include a health parameter data capturing module for reading the values form the medical devices and transmitting to the remote health monitoring station 108. According to an exemplary embodiment, the medical devices worn by the occupants may include but not limited to a Bluetooth or ZigBee or ZWave and the like.

In accordance with a non limiting exemplary embodiment of the present subject matter, the functional device 102 may be configured to receive an activation signal from one or authenticated mobile device 106a or from a personal computer 106b and to communicate the received activation signal with the automobile management module 104 either directly or indirectly through the functional device 102 to switch on the automobile or to customize the functionalities of the automobile. The functional device is further configured to transmit the functionalities and the operating status of the various embodiments of the automobile to the centralized server 110.

The functional device 102 may be configured to receive/relay signals like equipment status in automobile or activation signal from the authenticated mobile device 106a or from a personal computer 106b. A software application is configured in the mobile device 106a or from a personal computer 106b to transmit the activation signals to the functional device 102. The mobile device 106a may include a PDA, IPAD and the like. The signals may include voice signal, or text based signal or SMS like technology to customize the plurality of functional functionalities associated to the automobile. The functional device 102 further configured to receive/relay signals from a home automation server 112 which may be connected to different sensors at home for an automated operation of the gas system, garage door, window, security camera, fire, smoke sensors and the like home applications. The functional device may be a portable device, may be inbuilt in the automobile or can be hanged in the automobile through a suction means and the like.

Figure 2:
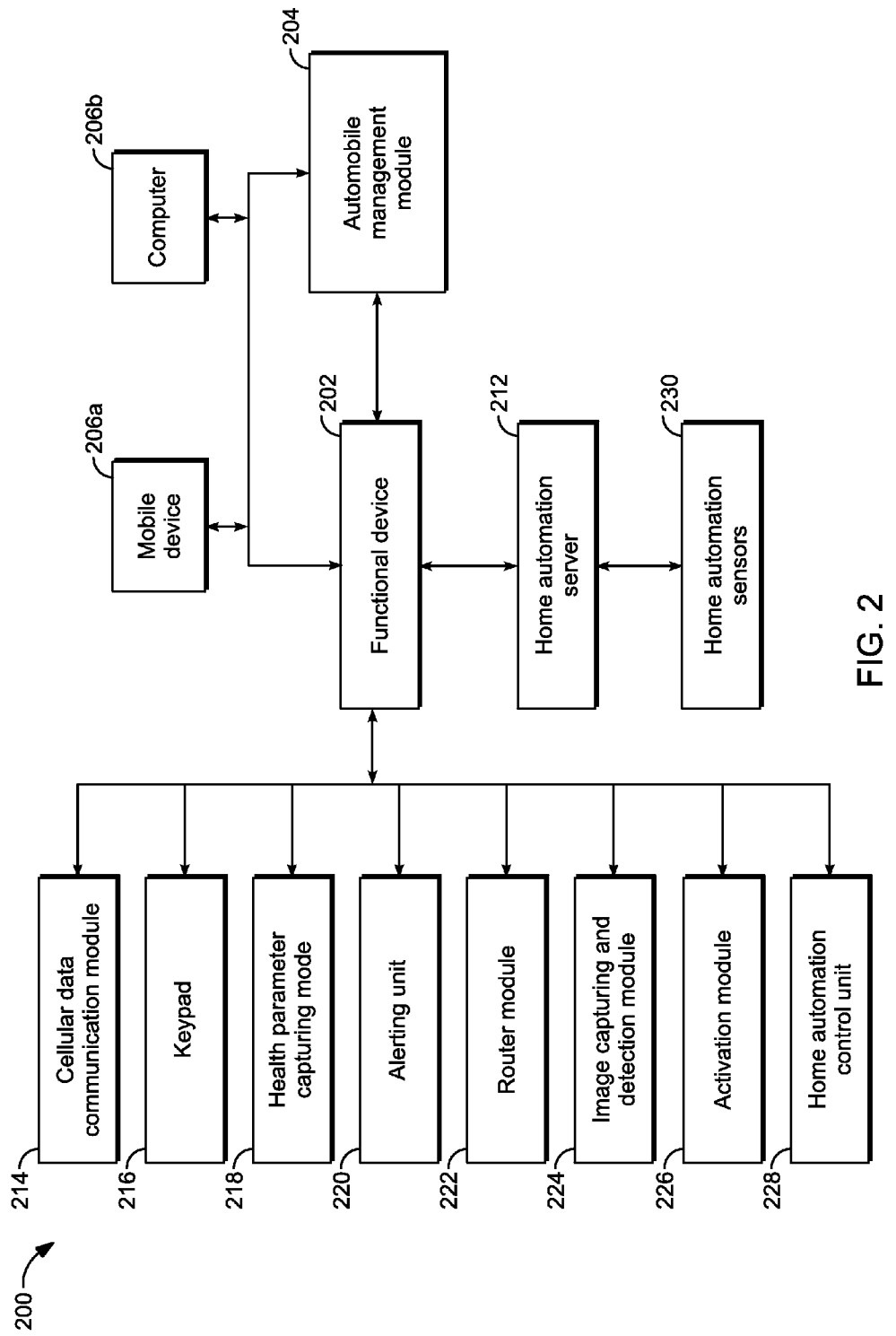
FIG. 2 is a diagram depicting an overview of a functional device with inbuilt modules.

Referring to FIG. 2 is a diagram 200 depicting an overview of a functional device with inbuilt modules. In accordance with a non limiting exemplary aspect of the present subject matter, the cellular data communication device 214 configured in the functional device enables a data communication among the functional device 202, the home automation server 212 and the automobile management module 204. The cellular data communication device 214 may include but not limited to a GPRS, WCDMA, EDGE, UMTS, HSDPA, Wi-Fi, WiMax or a GSM/CDMA device.

According to a non limiting exemplary embodiment of the present subject matter, the keypad 216 is configured in the functional device 202 for enabling the users to dial out a specific contact number and to speak to a person. The keypad 216 may be a physical keyboard or a virtual keyboard allowing the mobile devices to pair up with the functional device for accessing the internet or to enabling a data transfer from the automobile. The keypad 216 may further allow the users to send a text message and the like.

In accordance with a non limiting exemplary embodiment of the present subject matter, the health parameter data capturing module 218 reads the health parameters from one or more electronic gadgets worn by the occupants in the automobile and transmits to the health monitoring station. The health parameters may include but not limited to pulse rate, ECG, blood pressure, body temperature, heart rate, blood sugar, breath rate and the like. The cellular data communication device 214 in communication with the health parameter data capturing module 218 continuously monitors and transmits the captured health parameters to the health monitoring station.

According to a non limiting exemplary embodiment of the present subject matter, the alerting unit 220 is inbuilt in the functional device 202 for generating a voice based alerts for the occupants in the automobile. The alerts may include but not limited to alerting a name of the person driving the automobile, alerting the current location information, alerting the seating position of the driver, alerting the engine condition, alerting the fluid conditions, alerting the battery status, alerting the recent service date and due miles for servicing. The functional device 202 may be configured to upload the details like, levels of fluid conditions, the engine condition, the battery status, the recent service date and due miles for servicing details to the central server.

In accordance with a non limiting exemplary embodiment of the present subject matter, the router module 222 is configured in the functional device 202 for enabling the occupants in the automobile to access and surf the internet. This feature enables the functional device to be utilized as a wireless internet hub in the automobile.

According to a non limiting exemplary embodiment of the present subject matter, the image capturing and detection module 224 is inbuilt in the functional device 202 for identifying an image of the occupant and authorizing the occupant to communicate or talk with a doctor or a specialist at the remote health monitoring station. The image capturing and detection module 224 may include a camera and the like. The image capturing device and detection module 224 may also include a video conferencing device and the like.

In accordance with a non limiting exemplary embodiment of the present subject matter, the automobile activation module 226 inbuilt in the functional device 202 to operate the embodiments of the automobile and to customize the functional functionalities of the automobile. The automobile activation module 226 receives the automobile activation signal from the mobile device 206a or from a computer 206b configured with a software application and transmits the received signals to the automobile management module 204. The mobile device 206a and the personal computer are enabled to directly communicate with the automobile management module 226 for personalizing the settings of the automobile embodiments. The signals or commands may include but not limited to starting the automobile, turn the wipers on or turn on the heat during winter, adjust the seats, keep the doors open and the like.

According to a non limiting exemplary embodiment of the present subject matter, the home automation control unit 228 is configured to communicate with the home automation server 212 to receive/relay signals different home automation sensors 230 through the home automation server. The home automation sensors 230 may include but not limited to like gas, garage door, window, fire, smoke.

In accordance with a non limiting exemplary embodiment of the present subject matter, the router module 222 is configured in the functional device 202 to talk to the home automation server or read from the remote server. The home automation server 228 can communicate through internet, GPRS, WCDMA, EDGE, UMTS, HSDPA, Wi-Fi, WiMax or a GSM/CDMA, to get the real time status of the garage door, windows, doors, security system, gas leak, fire sensors, motion sensors and the like, status and operate those devices.

While specific embodiments of the invention have been shown and described in detail to illustrate the inventive principles, it will be understood that the invention may be embodied otherwise without departing from such principles.

The invention claimed is:

1. An interactive system for communicating health parameters of an occupant in an automobile and a dynamic operation of the automobile and home automation, the system comprising:
   a functional device configured to perform:
      reading and relaying a plurality of health parameters from at least one authorized occupant in the automobile;
      receive and relay a plurality of commands from the at least one authorized occupant for an automated operation of the automobile;
      reading and relaying a plurality of signals from a home automation server, whereby the home automation server connected to at least one sensor positioned at a predetermined location;
   a cellular data communication module inbuilt in the functional device for transmitting the plurality of health parameters to a remote health monitoring station over a communication network; and an automobile management module positioned in the automobile to operate the automobile and in communication with the functional device configured to customize a plurality of functional functionalities associated to the automobile, wherein the functional device is configured to receive or relay an automobile activation signal from a software application in an authenticated mobile device to customize the plurality of functional functionalities associated to the automobile.

2. The interactive system of claim 1, wherein the communication between the functional device and the automobile management module comprising at least one of a wired communication; and a short range wireless network.

3. The interactive system of claim 1, wherein the functional device comprising a key pad to dial a contact number.

4. The interactive system of claim 3, wherein the keypad enables to type a text based command.

5. The interactive system of claim 1, wherein the functional device configured to generate at least one alert corresponding to the plurality of functionalities associated to the automobile.

6. The interactive system of claim 1, wherein the functional device comprising an image capturing module to detect the at least one authorized occupant and communicate with the health monitoring station.

7. The interactive system of claim 1, where in the functional device inbuilt in the automobile.

8. The interactive system of claim 1, wherein the functional device configured to be hanged in an interior of the automobile.

9. The interactive system of claim 1, wherein the functional device configured to serve as a router enabling the at least one authorized occupant to access internet.

10. The interactive system of claim 1, wherein the functional device configured to transmit a functional status of a plurality of embodiments of the automobile to a centralized server.

11. The interactive system of claim 1, wherein the functional device comprising suction means to be held in the interior of the automobile.

12. The interactive system of claim 1, wherein the functional device configured to read health parameters from at least one medical device worn by the at least one occupant.

13. The interactive system of claim 1, wherein the at least one medical device communicates with the functional device through a short wireless network.

14. A functional device for communicating health parameters of an occupant in an automobile and a dynamic operation of the automobile and home automation, the device comprising:

a health parameter data capturing module for reading and relaying a plurality of health parameters from at least one authorized occupant in the automobile;

a cellular data communication module inbuilt in the functional device for transmitting the plurality of health parameters to a remote health monitoring station over a communication network;

a key pad to dial a contact number and to type a text based message;

an alerting unit configured to generate at least one alert corresponding to the plurality of functional functionalities associated to the automobile;

an image capturing module to detect the at least one authorized occupant and authenticating the at least one occupant to communicate with the health monitoring station;

a router module enabling the at least one authorized occupant to access an internet;

an automobile activation module configured to receive an activation signal from an authenticated mobile device to customize a plurality of functionalities associated to the automobile;

an automation control unit for reading and relaying a plurality of signals from a home automation server, whereby the home automation server connected to at least one sensor positioned at a predetermined location; and wherein the functional device is configured to receive or relay an automobile activation signal from a software application in an authenticated mobile device to customize the plurality of functionalities associated with the automobile.

15. The functional device of claim 14, wherein the keypad comprising a virtual keypad.

16. The functional device of claim 14, wherein the keypad comprising a physical keypad.

17. A method for communicating health parameters of an occupant in an automobile and a dynamic operation of the automobile and home automation, the method comprising:

reading and relaying a plurality of health parameters from at least one authorized occupant in the automobile, receiving and relaying a plurality of commands from the at least one authorized occupant for an automated operation of the automobile, reading and relaying a plurality of signals from a home automation server, whereby the home automation server is connected to at least one sensor positioned at a predetermined location by a functional device;

transmitting the plurality of health parameters to a remote health monitoring station over a communication network by a cellular data communication module inbuilt in the functional device;

receiving an activation signal, from a software application in an authenticated mobile device, by the functional device in an automobile module for customizing a plurality of functionalities associated to the automobile in communication with the functional device, whereby the automobile management device positioned in the automobile.

* * * * *